United States Patent
Hulin et al.

(12) 
(10) Patent No.: US 6,710,040 B1
(45) Date of Patent: Mar. 23, 2004

(54) FLUORINATED CYCLIC AMIDES AS DIPEPTIDYL PEPTIDASE IV INHIBITORS

(75) Inventors: Bernard Hulin, Essex, CT (US); Janice C. Parker, Ledyard, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/455,734

(22) Filed: Jun. 3, 2003

Related U.S. Application Data

(60) Provisional application No. 60/386,157, filed on Jun. 4, 2002.

(51) Int. Cl.[7] .................. C07D 205/04; C07D 207/04; C07D 211/06; A61K 31/397; A61K 31/40
(52) U.S. Cl. .................. 514/210.17; 514/315; 514/330; 514/423; 546/226; 546/245; 548/540; 548/953
(58) Field of Search .................. 546/226, 245; 548/540, 953; 514/210.17, 315, 330, 423

(56) References Cited

U.S. PATENT DOCUMENTS

| | | | |
|---|---|---|---|
| 5,939,560 A | 8/1999 | Jenkins et al. | 548/535 |
| 5,998,463 A | 12/1999 | Hulin et al. | 514/418 |
| 6,011,155 A * | 1/2000 | Villhauer | 544/333 |
| 6,124,305 A | 9/2000 | Villhauer | 514/272 |
| 6,166,063 A | 12/2000 | Villhauer | 514/423 |
| 6,172,081 B1 | 1/2001 | Damon | 514/307 |
| 6,303,661 B1 * | 10/2001 | Demuth et al. | 514/19 |
| 2002/0006899 A1 | 1/2002 | Pospisilik et al. | 514/2 |

FOREIGN PATENT DOCUMENTS

| | | | | |
|---|---|---|---|---|
| WO | WO9515309 | 6/1995 | ......... | C07D/207/16 |
| WO | WO9740832 | 11/1997 | ......... | A61K/31/425 |
| WO | WO9819998 | 5/1998 | ......... | C07D/207/00 |
| WO | WO9961431 | 12/1999 | ......... | C07D/277/04 |
| WO | WO0056296 | 9/2000 | ......... | A61K/31/00 |
| WO | WO0134594 | 5/2001 | ......... | C07D/401/06 |
| WO | WO0197808 | 12/2001 | ......... | A61K/21/425 |
| WO | WO02076450 | 10/2002 | ......... | A61K/31/40 |
| WO | WO03000255 | 1/2003 | ......... | A61K/31/4196 |

OTHER PUBLICATIONS

Neubert et al., Chemical Abstracts, 116:174775, 1992.*
Brandsch et al., European Journal of Biochemistry, 266(2), 502–508, 1999.*
Ashworth et al., Bioorganic & Medicinal Chem. Letters, vol. 6, No. 10, pp 1163–1166, 1996.
Augustyns et al., Eur. J. Med. Chem., 1997, 32, pp. 301–309.
Heghes et al., Biochemistry, 1999, 38, 11597–11603.
Holst et al., Diabetes, vol. 47, Nov. 98 pp. 1663–1670.
Ahren et al. European Jrnl of Pharmacology, 404, 2000, pp. 239–245.

* cited by examiner

*Primary Examiner*—Fiona T. Powers
(74) *Attorney, Agent, or Firm*—Peter C. Richardson; Gregg C. Benson; Robert T. Ronau

(57) ABSTRACT

The invention relates to new therapeutically active and selective inhibitors of the enzyme dipeptidyl peptidase-IV, pharmaceutical compositions comprising the compounds and the use of such compounds for treating diseases that are associated with proteins that are subject to processing by DPP-IV, such as Type 2 diabetes mellitus, hyperglycemia, impaired glucose tolerance, metabolic syndrome (Syndrome X or insulin resistance syndrome), glucosuria, metabolic acidosis, cataracts, diabetic neuropathy, diabetic nephropathy, diabetic retinopathy, diabetic cardiomyopathy, Type 1 diabetes, obesity, conditions exacerbated by obesity, hypertension, hyperlipidemia, atherosclerosis, osteoporosis, osteopenia, frailty, bone loss, bone fracture, acute coronary syndrome, infertility due to polycystic ovary syndrome, short bowel syndrome, anxiety, depression, insomnia, chronic fatigue, epilepsy, eating disorders, chronic pain, alcohol addiction, diseases associated with intestinal motility, ulcers, irritable bowel syndrome, inflammatory bowel syndrome and to prevent disease progression in Type 2 diabetes. The invention also relates to a method of identifying an insulin secretagogue agent for diabetes.

14 Claims, No Drawings

FLUORINATED CYCLIC AMIDES AS DIPEPTIDYL PEPTIDASE IV INHIBITORS

This application is filed claiming priority from co-pending U.S. Provisional Application No. 60/86157, filed Jun. 4, 2002.

FIELD OF THE INVENTION

The present invention relates to new therapeutically active and selective inhibitors of the enzyme dipeptidyl peptidase-IV (hereinafter "DPP-IV"), pharmaceutical compositions comprising the compounds and the use of such compounds for treating diseases that are associated with proteins that are subject to processing by DPP-IV, such as Type 2 diabetes, metabolic syndrome (Syndrome X or insulin resistance syndrome), hyperglycemia, impaired glucose tolerance, glucosuria, metabolic acidosis, cataracts, diabetic neuropathy, diabetic nephropathy, diabetic retinopathy, diabetic cardiomyopathy, Type 1 diabetes, obesity, hypertension, hyperlipidemia, atherosclerosis, osteoporosis, osteopenia, frailty, bone loss, bone fracture, acute coronary syndrome, infertility due to polycystic ovary syndrome, short bowel syndrome, anxiety, depression, insomnia, chronic fatigue, epilepsy, eating disorders, chronic pain, alcohol addiction, diseases associated with intestinal motility, ulcers, irritable bowel syndrome, inflammatory bowel syndrome and to prevent disease progression in Type 2 diabetes. The invention also relates to a method of identifying an insulin secretagogue agent for diabetes.

BACKGROUND OF THE INVENTION

Dipeptidyl peptidase-IV (EC 3.4.14.5) is a serine protease that preferentially hydrolyzes an N-terminal dipeptide from proteins having proline or alanine in the 2 position. The physiological role(s) of DPP-IV have not been fully elucidated, but it is believed to be involved in diabetes, glucose tolerance, obesity, appetite regulation, lipidemia, osteoporosis, neuropeptide metabolism and T-cell activation.

DPP-IV has been implicated in the control of glucose homeostasis because its substrates include the incretin peptides glucagon-like peptide 1 (GLP-1) and gastric inhibitory polypeptide (GIP). Cleavage of the N-terminal amino acids from these peptides renders them functionally inactive. GLP-1 has been shown to be an effective anti-diabetic therapy in Type 2 diabetic patients and to reduce the meal-related insulin requirement in Type 1 diabetic patients. GLP-1 and/or GIP are believed to regulate satiety, lipidemia and osteogenesis. Exogenous GLP-1 has been proposed as a treatment for patients suffering from acute coronary syndrome, angina and ischemic heart disease.

Administration of DPP-IV inhibitors in vivo prevents N-terminal degradation of GLP-1 and GIP, resulting in higher circulating concentrations of these peptides, increased insulin secretion and improved glucose tolerance. On the basis of these observations, DPP-IV inhibitors are regarded as agents for the treatment of Type 2 diabetes, a disease in which glucose tolerance is impaired. In addition, treatment with DPP-IV inhibitors prevents degradation of Neuropeptide Y (NPY), a peptide associated with a variety of central nervous system disorders, and Peptide YY which has been linked to gastrointestinal conditions such as ulcers, irritable bowel disease and inflammatory bowel disease.

In spite of the early discovery of insulin and its subsequent widespread use in the treatment of diabetes, and the later discovery of and use of sulfonylureas (e.g. chlorpropamide (Pfizer), tolbutamide (Upjohn), acetohexamide (E.I.Lilly)), biguanides (Phenformin (Ciba Geigy), metformin (G.D. Searle)) and thiazolidinediones (rosiglitazone (GlaxoSmithKline, Bristol-MyersSquibb), pioglitazone (Takeda, E.I.Lilly)) as oral hypoglycemic agents, the treatment of diabetes remains less than satisfactory.

The use of insulin, necessary in Type 1 diabetic patients and about 10% of Type 2 diabetic patients in whom currently available oral hypoglycemic agents are ineffective, requires multiple daily doses, usually by self-injection. Determination of the appropriate dosage of insulin necessitates frequent estimations of the glucose concentration in urine or blood. The administration of an excess dose of insulin causes hypoglycemia, with consequences ranging from mild abnormalities in blood glucose to coma, or even death.

Treatment of Type 2 diabetes usually comprises a combination of diet, exercise, oral agents, and in more severe cases, insulin. However, the clinically available hypoglycemics can have side effects which limit their use. A continuing need for hypoglycemic agents, which may have fewer side effects or succeed here others fail, is clearly evident.

Poorly controlled hyperglycemia is a direct cause of the multiplicity of complications (cataracts, neuropathy, nephropathy, retinopathy, cardiomyopathy) that characterize advanced diabetes mellitus. In addition, diabetes mellitus is a comorbid disease that frequently confounds hyperlipidemia, atherosclerosis and hypertension, adding significantly to the overall morbidity and mortality attributable to those diseases.

Epidemiological evidence has firmly established hyperlipidemia as a primary risk factor for cardiovascular disease ("CVD") due to atherosclerosis. Atherosclerosis is recognized to be a leading cause of death in the United States and Western Europe. CVD is especially prevalent among diabetic subjects, at least in part because of the existence of multiple independent risk factors such as glucose intolerance, left ventricular hypertrophy and hypertension in this population. Successful treatment of hyperlipidemia in the general population, and in diabetic subjects in particular, is therefore of exceptional medical importance.

Hypertension (or high blood pressure) is a condition that can occur in many patients in whom the causative agent or disorder is unknown. Such "essential" hypertension is often associated with disorders such as obesity, diabetes and hypertriglyceridemia, and it is known that hypertension is positively associated with heart failure, renal failure and stroke. Hypertension can also contribute to the development of atherosclerosis and coronary disease. Hypertension, together with insulin resistance and hyperlipidemia, comprise the constellation of symptoms that characterize Metabolic Syndrome, also known as insulin resistance syndrome ("IRS") and syndrome X.

Obesity is a well-known and common risk factor for the development of atherosclerosis, hypertension and diabetes. The incidence of obesity and hence of these diseases is increasing worldwide. Currently few pharmacological agents are available that reduce adiposity effectively and acceptably.

Osteoporosis is a progressive systemic disease characterized by low bone density and microarchitectural deterioration of bone tissue, with a consequent increase in bone fragility and susceptibility to fracture. Osteoporosis and the consequences of compromised bone strength are a significant cause of frailty, and of increased morbidity and mortality.

Heart disease is a major health problem throughout the world. Myocardial infarctions are a significant source of mortality among those individuals with heart disease. Acute coronary syndrome denotes patients who have or are at high risk of developing an acute myocardial infarction (MI).

Though there are therapies available for the treatment of diabetes, hyperglycemia, hyperlipidemia, hypertension, obesity and osteoporosis there is a continuing need for alternative and improved therapies.

SUMMARY OF INVENTION

This invention is directed to compounds of Formula I which are useful for the treatment of Type 2 diabetes, metabolic syndrome (Syndrome X or insulin resistance syndrome), hyperglycemia, impaired glucose tolerance, glucosuria, metabolic acidosis, cataracts, diabetic neuropathy, diabetic nephropathy, diabetic retinopathy, diabetic cardiomyopathy, Type 1 diabetes, obesity, hypertension, hyperlipidemia, atherosclerosis, osteoporosis, osteopenia, frailty, bone loss, bone fracture, acute coronary syndrome, infertility due to polycystic ovary syndrome, short bowel syndrome, anxiety, depression, insomnia, chronic fatigue, epilepsy, eating disorders, chronic pain, alcohol addiction, diseases associated with intestinal motility, ulcers, irritable bowel syndrome, inflammatory bowel syndrome and to prevent disease progression in Type 2 diabetes.

In particular, the invention is directed to a compound of the Formula I,

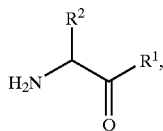

a prodrug thereof, or a pharmaceutically acceptable salt of the compound or the prodrug, wherein:

$R^1$ is 3-fluoroazetidin-1-yl, 3,3-difluoroazetidin-1-yl, 3,4-difluoropyrrolidin-1-yl, 3,3,4-trifluoropyrrolidin-1-yl, 3,3,4,4-tetrafluoropyrrolidin-1-yl, 3-fluoropiperidin-1-yl, 4-fluoropiperidin-1-yl, 3,4-difluoropiperidin-1-yl, 3,5-difluoropiperidin-1-yl, 3,3-difluoropiperidin-1-yl, 4,4-difluoropiperidin-1-yl, 3,4,5-trifluoropiperidin-1-yl, 3,3,4-rifluoropiperidin-1-yl, 3,3,5-trifluoropiperidin-1-yl, 3,4,4-trifluoropiperidin-1-yl, 3,3,4,5-tetrafluoropiperidin-1-yl, 3,4,4,5-tetrafluoropiperidin-1-yl, 3,3,4,4-tetrafluoropiperidin-1-yl, 3,3,5,5-tetrafluoropiperidin-1-yl, 3,3,4,5,5-pentafluoropiperidin-1-yl, 3,3,4,4,5-pentafluoropiperidin-1-yl or 3,3,4,4,5,5-hexafluoropiperidin-1-yl; and $R^2$ is $(C_1-C_8)$alkyl or $(C_3-C_8)$cycloalkyl.

In a preferred embodiment, the compound of Formula I is a compound wherein $R^1$ is 3-fluoroazetidin-1-yl or 3,3-difluoroazetidin-1-yl.

In another preferred embodiment, the compound of Formula I is a compound wherein $R^1$ is 3,4-difluoropyrrolidin-1-yl, 3,3,4-trifluoropyrrolidin-1-yl, 3,3,4,4-tetrafluoropyrrolidin-1-yl.

In another preferred embodiment, the compound of Formula I is a compound wherein $R^1$ is 3-fluoropiperidin-1-yl, 4-fluoropiperidin-1-yl, 3,4-difluoropiperidin-1-yl,3,5-difluoropiperidin-1-yl, 3,3-difluoropiperidin-1-yl or 4,4-difluoropiperidin-1-yl.

In another preferred embodiment, the compound of Formula I is a compound wherein $R^1$ is 3,4,5-trifluoropiperidin-1-yl, 3,3,4-trifluoropiperidin-1-yl, 3,3,5-trifluoropiperidin-1-yl, 3,4,4-trifluoropiperidin-1-yl, 3,3,4,5-tetrafluoropiperidin-1-yl, 3,4,4,5-tetrafluoropiperidin-1-yl, 3,3,4,4-tetrafluoropiperidin-1-yl 3,3,5,5-tetrafluoropiperidin-1-yl, 3,3,4,5,5-pentafluoropiperidin-1-yl, 3,3,4,4,5-pentafluoropiperidin-1-yl or 3,3,4,4,5,5-hexafluoropiperidin-1-yl.

In another preferred embodiment, the compound of Formula I is (2S,3S)-2-amino-3-methyl-1-(3,3,4,4-tetrafluoro-pyrrolidin-1-yl)-pentan-1-one hydrochloride;

(2S,3S)-2-amino-1-(3-fluoro-azetidin-1-yl)-3-methyl-pentan-1-one hydrochloride;

(S)-2-amino-2-cyclohexyl-1-(3,3,4,4-tetrafluoro-pyrrolidin-1-yl)-ethanone hydrochloride;

(2S,3R)-2-amino-3-methyl-1-(3,3,4,4-tetrafluoro-pyrrolidin-1-yl)-pentan-1-one hydrochloride;

(S)-2-amino-2-cyclohexyl-1-(3-fluoro-azetidin-1-yl)-ethanone hydrochloride;

(S)-2-amino-3-methyl-1-(3,3,4,4-tetrafluoro-pyrrolidin-1-yl)-butan-1-one hydrochloride;

(S)-2-amino-4-methyl-1-(3,3,4,4-tetrafluoro-pyrrolidin-1-yl)-pentan-1-one hydrochloride;

(S)-2-amino-2-cyclohexyl-1-(3,3-difluoro-azetidin-1-yl)-ethanone hydrochloride;

(2S,3S)-2-amino-1-(3,3-difluoro-azetidin-1-yl)-3-methyl-pentan-1-one hydrochloride;

(S)-2-amino-2-cyclohexyl-1-(4,4-difluoro-piperidin-1-yl)-ethanone hydrochloride;

(2S,3S)-2-amino-1-(4,4-difluoro-piperidin-1-yl)-3-methyl-pentan-1-one hydrochloride;

(S)-2-amino-1-(3,3,4,4-tetrafluoro-pyrrolidin-1-yl)-propan-1-one hydrochloride;

(S)-2-amino-1-(3,3-difluoro-azetidin-1-yl)-3-methyl-butan-1-one hydrochloride;

(S)-2-amino-1-(3-fluoro-azetidin-1-yl)-3-methyl-butan-1-one hydrochloride;

(2S,3R)-2-amino-1-(3-fluoro-azetidin-1-yl)-3-methyl-pentan-1-one hydrochloride;

(2S,3R)-2-amino-1-(3,3-difluoroazetidin-1-yl)-3-methyl-pentan-1-one hydrochloride;

(S)-2-amino-2-cyclopentyl-1-(3,3-difluoro-azetidin-1-yl)-ethanone hydrochloride;

(S)-2-amino-2-cyclopentyl-1-(3-fluoro-azetidin-1-yl)-ethanone hydrochloride; or (S)-2-amino-2-cyclopentyl-1-(3,3,4,4-tetrafluoro-pyrrolidin-1-yl)-ethanone hydrochloride.

In another preferred embodiment, the compound of Formula I,

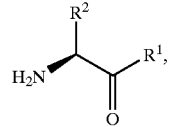

is a S enantiomer, as shown.

In another aspect, the invention is directed to a pharmaceutical composition comprising a therapeutically effective amount of a compound of Formula I as described above, a prodrug thereof or a pharmaceutically acceptable salt of the compound or the prodrug, and a pharmaceutically acceptable diluent or carrier.

In yet another aspect, the invention is directed to a pharmaceutical composition comprising a therapeutically effective amount of a first compound of Formula I as described above, a prodrug thereof or a pharmaceutically acceptable salt of said compound or said prordrug; and a second compound which is insulin or an insulin analog; insulinotropin; a biguanide; an $\alpha_2$-antagonist or an imidazoline; a glitazone; an aldose reductase inhibitor; a glycogen phosphorylase inhibitor; a sorbitol dehydrogenase inhibitor; a fatty acid oxidation inhibitor; an α-glucosidase inhibitor; a β-agonist; a phosphodiesterase inhibitor; a lipid-lowering agent; an antiobesity agent; vanadate, a vanadium complex or a peroxovanadium comiplex; an amylin antagonist; a glucagon antagonist; a growth hormone secretagogue; a gluconeogenesis inhibitor; a somatostatin analog; an inhibitor of renal glucose; or an antilipolytic agent; a prodrug of the second compound or a pharmaceutically acceptable salt of the second compound or of the prodrug of the second compound. In another embodiment of this aspect of the invention, the composition further comprises a pharmaceutically acceptable carrier or diluent.

In another aspect, the invention is directed to a kit comprising:

a) a first dosage form comprising a compound of Formula I as described above;

b) a second dosage form comprising an antidiabetic agent selected from insulin and insulin analogs; insulinotropin; biguanides; $\alpha_2$-antagonists and imidazolines; glitazones; aldose reductase inhibitors; glycogen phosphorylase inhibitors; sorbitol dehydrogenase inhibitors; fatty acid oxidation inhibitors; $\alpha$-glucosidase inhibitors; $\beta$-agonists; phosphodiesterase inhibitors; lipid-lowering agents; antiobesity agents; vanadate and vanadium complexes and peroxovanadium complexes; amylin antagonists; glucagon antagonists; growth hormone secretagogues; gluconeogenesis inhibitors; somatostatin analogs; inhibitors of renal glucose; antilipolytic agents; prodrugs of the second dosage form and pharmaceutically acceptable salts of the second dosage form and the prodrugs; and c) a container means for containing said first dosage (a) and said second dosage (b).

In one embodiment, the kit further comprising a pharmaceutically acceptable carrier or diluent and a container means for said carrier or diluent.

In another aspect, the inventino is directed to a therapeutic method of inhibiting dipeptidyl peptidase-IV in a mammal, the method comprising administering to said mammal in need of inhibition of dipeptidyl peptidase-IV a therapeutically effective amount of a compound of Formula I as described above, a prodrug thereof or a pharmaceutically acceptable salt of said compound or said prodrug; or of a pharmaceutical composition as described above.

In another aspect, the invention is directed to a therapeutic method of treating a condition mediated by dipeptidyl peptidase-IV inhibition in a mammal, the method comprising administering to said mammal suffering from a condition mediated by dipeptidyl peptidase-IV inhibition a therapeutically effective amount of a compound of Formula I as described above, a prodrug thereof or a pharmaceutically acceptable salt of said compound or said prodrug; or a pharmaceutical composition as described above.

In one embodiment of the methods, the condition treated is Type 2 diabetes, metabolic syndrome, hyperglycemia, impaired glucose tolerance, glucosuria, metabolic acidosis, cataracts, diabetic neuropathy, diabetic nephropathy, diabetic retinopathy, diabetic cardiomyopathy, Type 1 diabetes, obesity, a condition exacerbated by obesity, hypertension, hyperlipidemia, atherosclerosis, osteoporosis, osteopenia, frailty, bone loss, bone fracture, acute coronary syndrome, infertility due to polycystic ovary syndrome, disease progression in Type 2 diabetes, chronic fatigue, epilepsy, a disease associated with intestinal motility, ulcer, irritable bowel syndrome, inflammatory bowel syndrome, anxiety, depression, insomnia, chronic fatigue, epilepsy, an eating disorder, chronic pain or alcohol addiction.

In a preferred embodiment, the condition treated is Type 2 diabetes mellitus.

In another aspect, the invention is directed to a method of identifying whether an agent is a DPP-IV inhibitor, comprising:

a) administering the agent to a fasted, diabetic KK/H1J mouse;

b) challenging the KK/H1J mouse with oral glucose; and c) assessing a response in the mouse to a subsequent oral glucose challenge, wherein said agent may be identified as a treatment for Type 2 diabetes, metabolic syndrome, hyperglycemia, impaired glucose tolerance, glucosuria, metabolic acidosis, cataracts, diabetic neuropathy, diabetic nephropathy, diabetic retinopathy, diabetic cardiomyopathy, Type 1 diabetes, obesity, conditions exacerbated by obesity, hypertension, hyperlipidemia, atherosclerosis, osteoporosis, osteopenia, frailty, bone loss, bone fracture, acute coronary syndrome, infertility due to polycystic ovary syndrome, to prevent disease progression in Type 2 diabetes, anxiety, depression, insomnia, chronic fatigue, epilepsy, eating disorders, chronic pain, alcohol addiction, diseases associated with intestinal motility, ulcers, irritable bowel syndrome, inflammatory bowel syndrome or short bowel syndrome.

The term "alkyl" as used herein, means a saturated monovalent straight or branched aliphatic hydrocarbon radical having one to 8 carbon atoms.

The expression "pharmaceutically acceptable salt" as used herein in relation to compounds of Formula I of this invention includes pharmaceutically acceptable anionic salts. The term "pharmaceutically acceptable anion" refers to a negative ion that is compatible chemically and/or toxicologically with the other ingredients of a pharmaceutical composition and/or the animal being treated therewith. Suitable anions include, but are not limited to, halides (e.g., chloride, iodide, and bromide), $(C_1-C_{12})$alkylsulfonates (e.g., mesylate, ethylsulfonate, etc.), arylsulfonates (e.g., phenylsulfonate, tosylate, etc.), $(C_1-C_{12})$alkylphosphonates, $di(C_1-C_{12})$alkylphosphates (e.g., dimethylphosphate, diethylphosphate, ($\alpha$-diglycerol phosphate, etc.), arylphosphonates, arylphosphates, alkylarylphosphonates, alkylarylphosphates, $(C_1-C_2)$alkylcarboxylates (e.g., acetates, propionates, glutamates, glycerates, etc.), arylcarboxylates, and the like.

The compounds of the present invention may be isolated and used per se or in the form of its pharmaceutically acceptable salt, solvate and/or hydrate. The term "salts" refers to inorganic and organic salts of a compound of the present invention. These salts can be prepared in situ during the final isolation and purification of a compound, or by separately reacting the compound, or prodrug with a suitable organic or inorganic acid and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. See, e.g., Berge, et al., *J. Pharm. Sci.*, 66, 1–19 (1977).

The term "prodrug" means a compound that is transformed in vivo to yield a compound of Formula (I) or a pharmaceutically acceptable salt, hydrate or solvate of the compound. Such compounds include, but are not limited to, N-acyl and N-carboalkoxy derivatives of Formula I compounds, as well as imine derivatives. The transformation may occur via various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Some of the compounds described herein contain at least one stereogenic center; consequently, those skilled in the art will appreciate that all stereoisomers (e.g., enantiomers and diasteroisomers, and racemic mixtures thereof) of the compounds illustrated and discussed herein are within the scope of the present invention. In particular, the carbon that is substituted with $R^7$ in compounds of Formula I, and its intermediates, is stereogenic and these compounds are depicted and claimed in claim 1 as racemic mixtures and in claim 6 as the S enantiomers. One skilled in the art will also recognize that both the pyrrolidine and piperidine moieties of the compounds of Formula I may also contain at least one stereogenic center (e.g. Example 7). All stereoisomers (e.g., enantiomers and diasteroisomers, and racemic mixtures thereof) of these compounds claimed, illustrated and discussed herein are within the scope of the present invention.

Those skilled in the art will further recognize that the compounds of Formula I can exist in crystalline form as hydrates wherein molecules of water are incorporated within the crystal structure thereof and as solvates wherein molecules of a solvent are incorporated therein. All such hydrate and solvate forms are considered part of this invention.

This invention also includes isotopically-labeled compounds, which are identical to those described by Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen and fluorine, such as $^2H$, $^3H$, $^{13}C$, $^{14}C$, $^{15}N$, $^{18}O$, $^{17}O$, and $^{18}F$, respectively. Compounds of the present invention, prodrugs thereof, and pharmaceutically acceptable salts of the compounds or of the prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated (i.e., $^3H$), and carbon-14 (i.e., $^{14}C$), isotopes are particularly preferred for their ease of preparation and detectability. Further, substitution with heavier isotopes such as deuterium (i.e., $^2H$), can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the schemes and/or in the Examples below, by substituting a readily available isotopically labeled reagent for a non-isotopically labeled reagent.

DESCRIPTION OF INVENTION

In general, the compounds of Formula I of this invention may be prepared by methods that include processes known in the chemical arts, particularly in light of the description contained herein. Certain processes for the manufacture of the compounds of Formula I of this invention are illustrated by the following reaction schemes. Other processes are described in the experimental section. Some of the starting compounds for the reactions described in the schemes and Examples are prepared as illustrated herein. All other starting compounds may be obtained from general commercial sources, such as Sigma-Aldrich Corporation, St. Louis, Mo.

SCHEME I

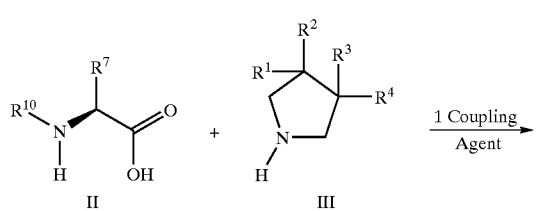

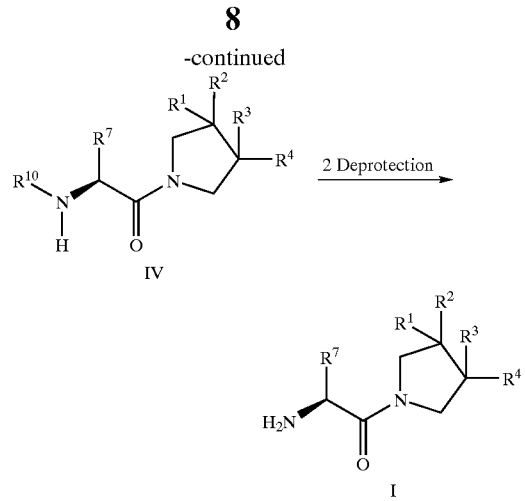

According to Scheme I, the compounds of Formula a, wherein $R^1$, $R^2$, $R^3$, $R^4$ and $R^7$ are defined above, may be prepared (Step 1) by coupling (L) amino acid compounds of Formula II (e.g., (L)-Boc-isoleucine, (L)-Boc-cyclohexylglycine, (L)-Boc-allo-isoleucine, (L)-Boc-leucine, (L)-Boc-valine or (L)-Boc-alanine), wherein $R^{10}$ is a nitrogen-protecting group compatible with the above-described chemical Scheme I, with a compound of Formula III, a fluorinated pyrrolidine, (e.g. 3,3-difluoropyrrolidine hydrochloride or 3,3,4,4-tetrafluoropyrrolidine hydrochloride).

Suitable nitrogen-protecting groups, $R^{10}$, may include for example, but are not limited to, tert-butoxycarbonyl ("Boc"), benzyloxycarbonyl and fluorenylmethoxycarbonyl ("Fmoc"). Other examples of nitrogen-protecting groups are described in "Protective Groups in Organic Synthesis", $2^{nd}$. Ed., P. G. M. Wuts and T. W. Greene, p.315, incorporated herein by reference. When the coupling is performed using a compound of Formula II, a compound of Formula IV is produced. A compound of Formula IV, in Step 2, may be dissolved in an inert solvent (e.g. ethyl acetate) and deprotected by methods appropriate to the nature of the $R^{10}$ group, as described in the reference cited above (e.g. gaseous acid if $R^{10}$ is Boc), providing a compound of Formula I.

The coupling reaction described above is readily accomplished by dissolving a compound of Formula II and a compound of Formula III in a reaction inert solvent (e.g. dichloromethane) in the presence of base (e.g. triethylamine or pyridine). To the resulting solution, is added a coupling agent or combination of coupling agents (e.g. hydroxybenzotriazole/1-(-3-dimethylaminopropyl)-3-ethylcarbodiimide hydrochloride). Other coupling agents may be utilized, such as 1-hydroxy-7-azabenzotriazole/1-(-3-dimethylaminopropyl)-3-ethylcarbodiimide hydrochloride, hydroxybenzotriazole/dicyclohexylcarbodiimide, 2-ethoxy-1-ethoxycarbonyl-1,2-dihydroquinoline, carbonyldiimidazole or diethylphosphorylcyanide. The coupling is conducted in an inert solvent, preferably an aprotic solvent. Suitable solvents include, for example, acetonitrile, dichloromethane, dimethylformamide, chloroform. For a discussion of other conditions useful for coupling carboxylic acids see Houben-Weyl, Vol XV, part II, E. Wunsch, Ed., G. Theime Verlag, 1974, Stuttgart, and those described in M. Bodansky, Principles of Peptide Synthesis, Springer-Verlag Berlin 1984, and The peptides. Analysis , Synthesis and Biology (ed. E. Gross and J. Meienhofer), vols 1–5 (Academic Press NY 1979–1983). The text of the above references are incorporated by reference.

The reaction is generally conducted at ambient pressure and temperature, until the starting materials are no longer present as determined by thin layer chromatography or other analytical techniques well known to those skilled in the art. The coupled product of Formula IV may be isolated according to methods well known to those skilled in the art.

Deprotection of a compound of Formula IV readily occurs by dissolving a compound of Formula IV in an inert solvent (e.g. ethyl acetate) and cooling to about 1° C., followed by treatment with gaseous acid (e.g. hydrochloric acid) for about 1 minute. The reaction mixture is stirred for about 15 minutes and then allowed to reach room temperature, followed by stirring for about an additional 30 minutes.

One of ordinary skill in the art will appreciate that the protected (L) amino acid compound of Formula II depicted in Scheme III, and exemplified in Examples 2–8, may be replaced with a racemic mixture of a compound of Formula II. Consequently, the compounds of Formula I may exist as racemic mixtures of enantiomers and these mixtures are within the scope of this invention.

As used herein, the term "inert solvent" is a solvent whose structure does not contain functional groups likely to interfere with the reaction. Examples for the activation of the hydroxyl groups and the coupling are dichloromethane, 1,2-dichloroethane, tetrahydrofuran (THF), dimethylformamide (DMF).

As used herein, the term "activating reagent" in this instance is one that transforms a hydroxyl group into a leaving group such as bromide, iodide, alkylsulfonate or arylsulfonate.

The optically active amino acids may be obtained by resolution or by asymmetric synthesis or by other methods well known to those skilled in the art, prior to coupling in Step 1 of Schemes III. Alternatively, resolution, if so desired, may be accomplished at a later point in the synthesis of the compounds of Formula I by techniques known to those of ordinary skill in the art.

Compound III of Scheme I may be prepared as known to those of ordinary skill in the art. For example, 3,3-difluoropyrrolidine hydrochloride may be prepared as described by Giardina, G et al. *Synlett*. 1995, 55. 3,3,4,4-tetrafluoropyrrolidine may be prepared as described in Chaudry et al. *J. Chem. Soc.*, 1964, 874. Alternatively, 3,3,4,4-tetrafluoropyrrolidine may be prepared as depicted below in Scheme II.

SCHEME II

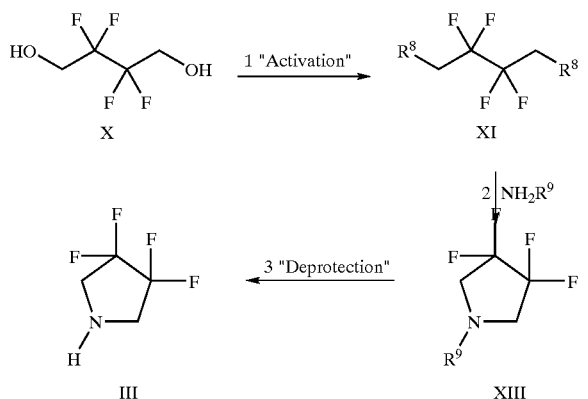

According to Scheme II, in Step 1, the hydroxyl groups of 2,2,3,3-tetrafluorobutanediol (X) are activated to a leaving group, $R^8$, (wherein $R^8$ may be Br, I or $SO_2R^{11}$, wherein $R^{11}$ may either be (1) a $C_1$–$C_8$ straight or branched alkyl, optionally substituted with one or several fluorines or (2) an aryl group, optionally substituted with halogen or a $C_1$–$C_8$ straight or branched alkyl optionally substituted with one to four fluorines). Preferably, however, $R^8$ is a trifluoromethylsulfonyloxy radical ($F_3CSO_3$). The activating reagents necessary to transform the alcohol function to, for example, bromine or iodine are well-known to those skilled in the art (see e.g. March, Advanced Organic Chemistry, $3^{rd}$ ed. pp. 382–384 and Larock, Comprehensive Organic Transformations, pp. 353–360, incorporated by reference) and include, but are not limited to, the following activating reagents: hydrogen bromide ("HBr"), phosphorus tribromide ("$PBr_3$"), phosphorus pentabromide ("$PBr_5$"), thionyl bromide ("$SOBr_2$") and hydrogen iodide ("HI"). Preferred activating reagent combinations are triphenylphosphine/carbon tetrabromide ("$Ph_3P/CBr_4$"), $Ph_3P$/N-bromosuccinimide, potassium iodide/phosphoric acid ("KI/$H_3PO_4$"), $Ph_3P/I_2$ and $Me_3SiCl/NaI$. Activation of the alcohol function to an alkyl or arylsulfonate is accomplished by reaction with the corresponding sulfonyl chloride or sulfonic anyhydride in an inert solvent in the presence of a base, such as pyddine or triethylamine, which is cooled (0° C.) and stirred for about one hour. The reaction mixture is then stirred at room temperature for about an additional hour.

In Step 2, the reaction of compound XI with a primary amine $R^9NH_2$, wherein $R^9$ is an alkyl or aryl "protecting" group (i.e., such that the bond linking $R^9$ to the nitrogen atom may be easily cleaved by standard chemical manipulation known to those skilled in the art in Step 3), is accomplished by heating the solution to reflux overnight. Examples of N-protecting groups are described in "Protective Groups in Organic Synthesis", $2^{nd}$. Ed., P. G. M. Wuts and T. W. Greene, p.362, incorporated herein by reference, and include, for example, benzyl, tert-butyl, allyl and benzhydryl. Preferably, $R^9$ is benzyl, in which case the deprotection, Step 3, is performed by hydrogenolysis in the presence of palladium.

Step 3 can be performed on a cationic salt of intermediate compound XII, such as hydrochloride, hydrobromide, acetate, trifluoroacetate etc., in an appropriate solvent (e.g. water, methanol or ethanol). Removal of the $R^9$ protecting group from compound XII may be accomplished under conditions appropriate for the particular $R^9$ protecting group in use. Such conditions include, for example, (a) hydrogenolysis where $R^9$ is benzyl or benzhydryl; (b) treatment with a strong acid, such as trifluoroacetic acid or hydrochloric acid, wherein $R^9$ is tert-butyl; or (c) treatment with tributyltinhydride and acetic acid in the presence of catalytic bis(triphenylphosphine) palladium (II) chloride where $R^9$ is allyl.

If $R^9$ is benzyl, deprotection is performed by hydrogenolysis in the presence of 10% palladium in ethanol at about 45 psi for about 3 hours. The final compound III is, thus, isolated as the corresponding cationic salt by filtration of the catalyst over diatomaceous earth, removal of the solvent and trituration with a non-hydroxylic solvent, such as diethyl ether, diisopropyl ether, ethyl acetate, 1,4-dioxane or tetrahydrofuran. Compound III is utilized, as described above in Scheme I, for preparation of DPP-IV inhibitor compounds of Formula I.

SCHEME III

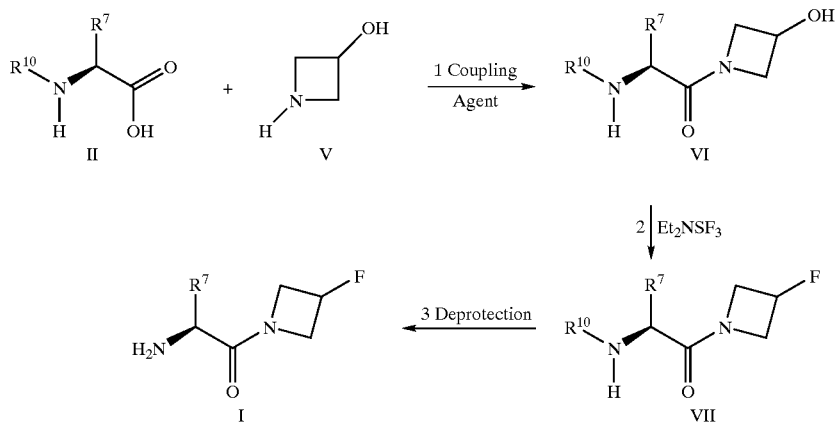

Alternatively, compounds of Formula I, wherein a and b are each 0, may be prepared in accordance with the steps of Scheme III. In Step 1 of Scheme III, (L) amino acid compound of Formula II (e.g. (L)-Boc-isoleucine), wherein $R^7$ and $R^{10}$ are defined above, is coupled with hydroxyazetidine (the compound of Formula V), as analogously described above in step 1 of Scheme I, forming a compound of Formula VI. The resulting compound of Formula VI is treated, in Step 2, with diethylaminosulfur trifluoride or a similar fluorinating agent, providing a compound of Formula VII. In Step 3, a compound of Formula VII is treated with acid, as analogously described above in Step 2 of Scheme I, providing a compound of Formula I, wherein a and b are each zero.

The reaction described in Step 2 is readily accomplished by cooling a solution of diethylaminosulfur trifluoride (e.g. −78° C.) in a reaction inert solvent (e.g. dichloromethane) to which a solution of the compound of Formula VI is added dropwise. The reaction mixture is warmed to ambient temperatures, until the starting materials are no longer present or until the reaction is completed, as determined by thin layer chromatography or other analytical techniques well known to those skilled in the art. The compound of Formula VII may be isolated according to methods well known to those skilled in the art and further treated with gaseous acid in Step 3, as analogously described above in Step 2 of Scheme I.

Similarly, monofluoro pyrrolidine and piperidine derivatives can be prepared by a similar sequence, starting respectively with pyrrolidin-3-ol or a hydroxypiperidine.

SCHEME IV

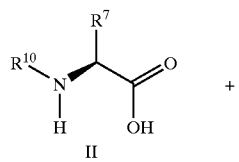

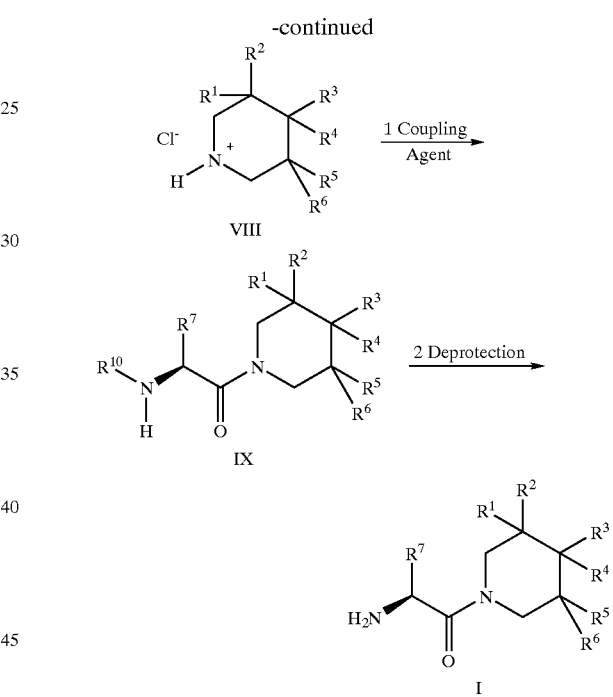

Alternatively, compounds of Formula I can be prepared according to Scheme IV. In Step 1, (L) amino acid compounds of Formula II (e.g. (L)-Boc-isoleucine, Boc-cyclohexylglycine etc.), wherein $R^7$ and $R^{10}$ are defined above, may be coupled with a compound of Formula VIII, a fluorinated piperidine, wherein $R^1$, $R^2$, $R^3$, $R^4$, $R^5$ and $R^6$ are defined above, (e.g. 4,4-difluoro-piperidine hydrochloride), as analogously described above in Step 1 of Scheme I, forming the compound of Formula IX. The compound of Formula IX, in Step 2, may be deprotected (e.g. gaseous acid), as analogously described in Step 2 of Scheme I, providing the compound of Formula I.

It will be recognized by a person skilled in the art that the synthetic sequence used in Schemes I and 4 can be applied to the synthesis of analogous compounds containing an azetidine ring in lieu of the pyrrolidine or piperidine moiety, starting with the requisite azetidine starting material.

One of ordinary skill in the art will appreciate that the protected (L) amino acid compounds of Formula II depicted in Schemes I, 3 and 4, and exemplified in Examples 1–16, may be replaced with a racemic mixture of a compound of Formula II. Consequently, the compounds of Formula I may exist as racemic mixtures of enantiomers and these mixtures are within the scope of this invention.

The optically active amino acids may be obtained by resolution or by asymmetric synthesis or by other methods well known to those skilled in the art, prior to coupling in Step 1 of Schemes I, III and IV. Alternatively, resolution, if so desired, may be accomplished at a later point in the synthesis of the compounds of Formula I by techniques known to those of ordinary skill in the art.

The compounds of Formula I of the present invention are useful for the treatment of dipeptidyl peptidase-IV related conditions; the treatment of type II diabetes; the prevention of disease progression in type II diabetes; the treatment of type I diabetes, impaired glucose tolerance, hyperglycemia, impaired glucose tolerance, metabolic syndrome (Syndrome X or insulin resistance syndrome), glucosuria, metabolic acidosis, cataracts, diabetic neuropathy and nephropathy, Metabolic Syndrome, obesity, the treatment of hypertension, hyperlipidemia, metabolic acidosis, arthritis, osteoporosis, osteopenia, frailty, bone loss, bone fracture, short stature due to growth hormone deficiency, infertility due to polycystic ovary syndrome, anxiety, depression, insomnia, chronic fatigue, epilepsy, eating disorders, chronic pain, alcohol addiction, diseases associated with intestinal motility, ulcers, irritable bowel syndrome, inflammatory bowel syndrome and short bowel syndrome.

The invention also relates to therapeutic methods for treating or preventing the above described conditions in a mammal, including a human, wherein a compound of Formula I of this invention is administered as part of an appropriate dosage regimen designed to obtain the benefits of the therapy. The appropriate dosage regimen, the amount of each dose administered and the intervals between doses of the compound will depend upon the compound of Formula I of this invention being used, the type of pharmaceutical compositions being used, the characteristics of the subject being treated and the severity of the conditions.

In general, an effective dosage for the compounds of Formula I described above is in the range of 0.01 mg/kg/day to 30 mg/kg/day, preferably 0.01 mg/kg/day to 1 mg/kg/day in single or divided doses. Some variation in dosage will necessarily occur, however, depending on the condition of the subject being treated. The individual responsible for dosing will, in any event, determine the appropriate dose for the individual subject.

The compounds of Formula I of this invention may be administered to a subject in need of treatment by a variety of conventional routes of administration, including orally and parenterally, (e.g., intravenously, subcutaneously or intramedullary). Further, the pharmaceutical compositions of this invention may be administered intranasally, as a suppository or using a "flash" formulation, i.e., allowing the medication to dissolve in the mouth without the need to use water.

The compounds of this invention may be administered in single (e.g., once daily) or multiple doses or via constant infusion. The compounds of this invention may also be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the compounds of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like.

Thus, for purposes of oral administration, tablets containing various excipients such as sodium citrate, calcium carbonate and/or calcium phosphate may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the active pharmaceutical agent therein may be combined with various sweetening or flavoring agents, coloring matter or dyes and, if desired, emulsifying or suspending agents, together with diluents such as water, ethanol, propylene glycol, glycerin and/or combinations thereof.

For parenteral administration, solutions of the compounds of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insufflator may be formulated containing a powder mix of a compound or compounds of the invention and a suitable powder base such as lactose or starch.

Since the present invention has an aspect that relates to treatment of the above-described indications by treatment with a combination of compounds that may be co-administered separately, the invention also relates to combining separate pharmaceutical compositions in kit form. The kit comprises two separate compositions: (1) a first dosage form comprising.a compound of Formula I, a prodrug thereof, or pharmaceutically acceptable salts and prodrugs, plus a pharmaceutically acceptable diluent or carrier; and (2) a second dosage form comprising an antidiabetic agent selected from insulin and insulin analogs; insulinotropin; biguanides; $\alpha_2$-antagonists and imidazolines; glitazones; aldose reductase inhibitors; glycogen phosphorylase inhibitors; sorbitol dehydrogenase inhibitors;

fatty acid oxidation inhibitors; α-glucosidase inhibitors; β-agonists; phosphodiesterase inhibitors; lipid-lowering agents; antiobesity agents; vanadate and vanadium complexes and peroxovanadium complexes; amylin antagonists; glucagon antagonists; growth hormone secretagogues; gluconeogenesis inhibitors; somatostatin analogs; inhibitors of renal glucose; antilipolytic agents; prodrugs of the second dosage form and pharmaceutically acceptable salts of the second dosage form and the prodrugs, plus a pharmaceutically acceptable carrier or diluent.

The amounts of (1) and (2) are such that, when co-administered, the conditions, as described above, is treated or remediated. The kit comprises a container for containing the separate dosage forms, such as a divided bottle or a divided foil packet, wherein each compartment contains a plurality of dosage forms (e.g. tablets) comprising (1) or (2). Alternatively, rather than separating the active ingredient-containing dosage forms, the kit may contain separate compartments, each of which contains a whole dosage that in turn comprises separate dosage forms.

An example of this type of kit is a blister pack wherein each individual blister contains two (or more) tablet(s) comprising pharmaceutical composition dosage form (1), and dosage form (2). Typically, the kit comprises directions to the administration of the separate components. The kit form is particularly advantageous when the separate components are preferably administered in different dosage forms (e.g. oral and parenteral), are administered at different dosage intervals, or when titration of the individual components of the combination is desired by the prescribing physician.

In the case of the instant invention, a kit, therefore, comprises:

d) a first dosage form comprising a compound of Formula 1, a prodrug thereof, or a pharmaceutically acceptable salt or prodrug;

e) a second dosage form comprising an antidiabetic agent selected from insulin and insulin analogs; insulinotropin; biguanides; $\alpha_2$-antagonists and imidazolines; glitazones; aldose reductase inhibitors; glycogen phosphorylase inhibitors; sorbitol dehydrogenase inhibitors; fatty acid oxidation inhibitors; α-glucosidase inhibitors; β-agonists; phosphodiesterase inhibitors; lipid-lowering agents; antiobesity agents; vanadate and vanadium complexes and peroxovanadium complexes; amylin antagonists; glucagon antagonists; growth hormone secretagogues; gluconeogenesis inhibitors; somatostatin analogs; inhibitors of renal glucose; antilipolytic agents; prodrugs of the second dosage form and pharmaceutically acceptable salts of the second dosage form and the prodrugs;

f) an optional pharmaceutically acceptable carrier or diluent; and g) a container means for containing said first dosage (a), said second dosage (b) and said optional carrier or diluent (c).

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easton, Pa., 19th Edition (1995).

In Vitro Assay for Dioeotidyl Peotidase Inhibition

The dipeptidyl peptidase inhibition may be demonstrated in vitro by the following assay, which is adapted from published methods for the measurement of DPP-IV activity (Assay of dipeptidyl peptidase IV in serum by fluorometry of 4-methoxy-2-naphthylamide. (1988) Scharpe, S., DeMeester, I., Vanhoof, G., Hendriks, D., Van Sande, M., Van Camp, K. and Yaron, A. Clin. Chem. 34:2299–2301; Dipeptidyl peptidases of human lymphocytes (1988) Lodja, Z. Czechoslovak Medicine, 11: 181–194.) Substrate solution, comprising 50 μM Gly-Pro4-methoxy B naphthylamide HCl (e.g. 182 μg Gly-Pro4-methoxy B naphthylamide HCl per 10 mL 50 mM Tris assay buffer pH 7.3 containing 0.1M sodium chloride, 0.1% (v/v) Triton and enzyme (Enzyme Systems Products Cat#SPE-01, DPP-IV 5 mU/mL stock) diluted 1:100 (100 μL enzyme per 10 mL substrate solution), forming an enzyme substrate solution that is maintained at 4° C. 150 μL of the enzyme substrate solution is pipetted into microtiter wells of a polystyrene 96-well plate, and maintained at 4° C. 5 μL/well of compounds of Formula I are added, bringing the final compound of Formula I concentrations to 3 μM–10 nM per well.

Controls. Enzyme is omitted from four (4) wells, as a reagent blank. 5 μL of 3 mM Diprotin A is added to four wells as a positive quality control, providing a final Diprotin A concentration of 100 μM. To measure total enzyme activity (i.e. a negative control), without the influence of any compounds of Formula I, 5 μL of distilled water is added to four wells.

The entire assay is incubated overnight (about 14–18 hours) at 37° C. The reaction is quenched by adding 10 μL of Fast Blue B solution (0.5 mg/mL Fast Blue B in a buffer comprising 0.1M sodium acetate pH 4.2 and 10% (v/v) Triton X-100 to each well, followed by shaking for approximately 5 minutes at room temperature. The plates may be analyzed on a Spectramax spectrophotometer, or equivalent equipment, (absorption maximum at 525 nm). $IC_{50}$ data for compounds may be obtained by measuring the activity of DPP-IV over a range of compound concentrations from 10 nM to 3 μM.

Oral glucose tolerance tests ("OGTT") have been in use in humans since, at least, the 1930's, Pincus et al., Am. J. Med. Sci, 188: 782 (1934), and is routinely used in the diagnosis of human diabetes, though, not to evaluate the efficacy of therapeutic agents in patients.

KK mice have been used to evaluate glitazones (Fujita et al. Diabetes 32:804–810 (1983); Fujiwara et al., Diabetes 37: 1549–48 (1988); Izumi et al. Biopharm Durg. Dispos. 18:247–257 (1997)), metformin (Reddi et al. Diabet. Metabl. 19:44–51 (1993)), glucosidase inhibitors (Hamada et al. Jap. Pharmacol. Ther. 17:17–28 (1988); Matsuo et al. Am. J. Clin. Nutr. 55:314S–317S (1992)), and the extra-pancreatic effects of sulfonylureas (Kameda et al Arzenim. Forsch./Drug Res. 32:39044 (1982); Muller et al. Horm. Metabl. Res. 28:469–487 (199)).

KK mice are derived from an inbred line first established by Kondo et al. (Kondo et al. Bull. Exp. Anim. 6:107–112 (1957)). The mice spontaneously develop a hereditary form of polygenic diabetes that progresses to cause renal, retinal and neurological complications analogous to those seen in human diabetic subjects, but they do not require insulin or other medication for survival.

The invention is directed to the use of KK mice to evaluate the effects of insulin secretagogue agents in the context of an oral glucose tolerance test.

In Vivo Assay for Glucose Lowering

The glucose lowering effects of DPP-IV inhibitors, compounds of Formula I, may be exemplified in 4–6 week old KK/H1J mice (Jackson Labs) in the context of an oral glucose tolerance test. The mice are fasted overnight (about 14–18 hours), but allowed free access to water. After fasting, (time ("t"=0), 25 μL of blood is drawn from the retro-orbital sinus and added to 0.025% heparinized saline (100 μL) on ice. The mice (10 per group) are then orally dosed with a solution of a compound of Formula I in 0.5% methylcellulose (0.2 mumouse). Two controls groups receive only 0.5% methylcellulose. At t=15 minutes, the mice are bled, as described above, and then dosed with 1 mg/kg glucose in distilled water (0.2 mumouse). The first control group is dosed with glucose. The second control group is dosed with water. At t=45 minutes, the mice are again bled, as described above. The blood samples are centrifuged, the plasma collected and analyzed for glucose content on a Roche-Hitachi 912 glucose analyzer. The data may be expressed as percent (%) inhibition of glucose excursion relative to the two control groups (i.e. the glucose level in the animals receiving glucose but no test compound representing 0% inhibition and the glucose concentration in the animals receiving only water representing 100% inhibition).

GENERAL EXPERIMENTAL PROCEDURES

Melting points were determined on a Thomas Scientific capillary melting point apparatus, and are uncorrected.

Flash chromatography was performed according to the method described by W. C. Still et al. in *J. Org. Chem.* 1978, 43, 2923.

The examples below are intended to illustrate particular embodiments of the invention and are not intended to limit the specification, including the claims, in any manner. The compounds exemplified hereinafter, Examples 1–16, displayed in vitro activity with an $IC_{50}$ (concentration of test compound required for 50% inhibition) of at or below 3 μM.

Example 1

(2S,3S)-2-Amino-3-methyl-1-(3,3,4,4-tetrafluoro-pyrrolidin-1-yl)-pentan-1-one

Step 1: [F(1S,2S)-2-Methyl-1-(3,3,4,4-tetrafluoro-pyrrolidine-1-carbonyl)-butyl]-carbamic Acid tert-Butyl Ester.

To a mixture of (L)-Boc-isoleucine (322 mg, 1.30 mmol), 3,3,4,4-tetrafluoro-pyrrolidine hydrochloride (300 mg, 1.67 mmol), hydroxybenzotriazole (225 mg, 1.67 mmol) and triethylamine (0.23 mL, 1.67 mmol) in dichloromethane (10 mL) was added 1-(-3-dimethylaminopropyl)-3-ethylcarbodiimide hydrochloride (319 mg, 1.67 mmol). The mixture was stirred at room temperature overnight, diluted with ethyl acetate, washed with 2 N HCl, saturated sodium bicarbonate solution, water and brine, dried over magnesium sulfate and concentrated. The product was purified by flash-chromatography (hex/ethyl acetate, 4:1) and isolated as a white solid (415 mg, 86%).

The 3,3,4,4-tetrafluoro-pyrrolidine hydrochloride utilized in Step 1 may be prepared according to Chaudhry et al. *J. Chem.Soc.*; 1964; 874. Alternatively, the fluorinated pyrrolidine may be prepared as described in Scheme II.

Step 2: (2S,3S)-2-Amino-3-methyl-1-(3,3,4,4-tetrafluoro-pyrrolidin-1-yl)-pentan-1-one Hydrochloride.

[(1S, 2S)-2-Methyl-1-(3,3,4,4-tetrafluoro-pyrrolidine-1-carbonyl)-butyl]-carbamic acid tert-butyl ester (200 mg, 0.56 mmol) was dissolved in ethyl acetate (4 mL), cooled to ° C. and treated with gaseous HCl for about 1 minute. After 15 minute at 0° C. and 30 minute at room temperature, the mixture was concentrated to dryness and the solid was triturated with hexane, collected and dried under vacuum overnight (124 mg, 76%, mp>250° C.).

Example 2

(2S,3S)-2-Amino-1-(3-fluoro-azetidin-1-yl)-3-methyl-pentan-1-one

Step 1: [(1S,2S)-1-(3-Hydroxy-azetidine-1-carbonyl)-2-methyl-butyl]-carbamic Acid tert-Butyl Ester.

[(1S, 2S)-1-(3-Hydroxy-azetidine-1-carbonyl)-2-methyl-butyl]-carbamic acid tert-butyl ester was prepared as analogously described in Step 1 of Example 1 from a mixture of (L)-Boc-isoleucine and 3-hydroxyazetidine. 3-Hydroxyazetidine was prepared according to Lee, J. et al. (*Bioorg.Med.Chem.Lett.* 2000, 10, 1063).

Step 2: [(1S,2S)-1-(3-Fluoro-azetidine-1-carbonyl)-2-methyl-butyl]-carbamic Acid tert-Butyl Ester.

To a cooled (−78° C.) solution of diethylaminosulfur trifluoride (0.46 mL, 3.5 mmol) in dichloromethane (6 mL), was added dropwise a solution of [(1S,2S)-1-(3-hydroxy-azetidine-1-carbonyl)-2-methyl-butyl]-carbamic acid tert-butyl ester (1.0 g, 3.5 mmol) in dichloromethane (4 mL). The mixture was warmed to room temperature, stirred overnight, then diluted with ethyl acetate and poured into ice/water. The layers were separated, and the organic phase washed with water and brine, dried over magnesium sulfate and concentrated. The product was purified by flash-chromatography (ethyl acetate) and isolated as an oil (250 mg, 25%).

Step 3: (2S,3S)-2-Amino-1-(3-fluoro-azetidin-1-yl)-3-methyl-pentan-1-one.

(2S,3S)-2-amino-1-(3-fluoro-azetidin-1-yl)-3-methyl-pentan-1-one was prepared by HCl treatment of [(1S,2S)-1-(3-fluoro-azetidine-1-carbonyl)-2-methyl-butyl]-carbamic acid tert-butyl ester as analogously described in Step 2 of Example 1. (mp 208–210° C.).

Example 3

(S)-2-Amino-2-cyclohexyl-1-(3,3,4,4-tetrafluoro-pyrrolidin-1-yl)-ethanone

Step 1: (S)-[1-Cyclohexyl-2-oxo-2-(3,3,4,4-tetrafluoro-pyrrolidin-1-yl)-ethyl]-carbamic Acid tert-Butyl Ester.

(S)-[1-Cyclohexyl-2-oxo-2-(3,3,4,4-tetrafluoro-pyrrolidin-1-yl)-ethyl]-carbamic acid tert-butyl ester was prepared from (L)-Boc-cyclohexylglycine and 3,3,4,4-tetrafluoropyrrolidine as analogously described in Step 1 of Example 1.

Step 2: (S)-2-Amino-2-cyclohexyl-1-(3,3,4,4-tetrafluoro-pyrrolidin-1-yl)-ethanone.

(S)-2-amino-2-cyclohexyl-1-(3,3,4,4-tetrafluoro-pyrrolidin-1-yl)-ethanone was obtained by HCl treatment of (S)-[1-cyclohexyl-2-oxo-2-(3,3,4,4-tetrafluoro-pyrrolidin-1-yl)-ethyl]-carbamic acid tert-butyl ester as analogously described in Step 2 of Example 1. (mp 278° C.).

Example 4

(2S,3R)-2-Amino-3-methyl-1-(3,3,4,4-tetrafluoro-pyrrolidin-1-yl)-pentan-1-one

Step 1: [(1S,2R)-2-Methyl-1-(3,3,4,4-tetrafluoro-pyrrolidine-1-carbonyl)-butyl]-carbamic Acid tert-Butyl Ester.

[(1S,2R)-2-Methyl-1-(3,3,4,4-tetrafluoro-pyrrolidine-1-carbonyl)-butyl]-carbamic acid tert-butyl ester was prepared as analogously described in Step 1 of Example 1 from (L)-Boc-allo-isoleucine and 3,3,4,4-tetrafluoropyrrolidine.

Step 2: (2S,3R)-2-Amino-3-methyl-1-(3,3,4,4-tetrafluoro-pyrrolidin-1-yl)-pentan-1-one (2S,3R)-2-amino-3-methyl-1-(3,3,4,4-tetrafluoro-pyrrolidin-1-yl)-pentan-1-one was prepared by HCl treatment of [(1S,2R)-2-methyl-1-(3,3,4,4-tetrafluoro-pyrrolidine-1-carbonyl)-butyl]-carbamic acid tert-butyl ester as analogously described in Step 2 of Example 1. (mp>250° C.).

Example 5

(S)-2-Amino-2-cyclohexyl-1-(3-fluoro-azetidin-1-yl)-ethanone (S)-2-amino-2-cyclohexyl-1-(3-fluoro-azetidin-1-yl)-ethanone was synthesized from 3-azetidinol hydrochloride and (L)-Boc-cyclohexylglycine as analogously described in Example 2 (mp 238–240° C.).

Example 6

(S)-2-Amino-3-methyl-1-(3,3,4,4-tetrafluoro-pyrrolidin-1-yl)-butan-1-one (S)-2-amino-3-methyl-1-(3,3,4,4-tetrafluoro-pyrrolidin-1-yl)-butan-1-one was prepared from (L)-Boc-valine and 3,3,4,4-tetrafluoropyrrolidine as analogously described in Example 1 (mp 234–238° C.).

Example 7

(2S,3R)-2-Amino-1-(3,3-difluoro-pyrrolidin-1-yl)-3-methyl-pentan-1-one (2S,3R)-2-amino-1-(3,3-difluoro-pyrrolidin-1-yl)-3-methyl-pentan-1-one was prepared from 3,3-difluropyrrolidine hydrochloride (prepared according to Giardina, G. *Synlett* 1995, 55) and (L)-Boc-isoleucine, as analogously described in Example 1 (mp 196–198° C.).

Example 8

(2S,3S)-2-Amino-1-(3,3-difluoro-pyrrolidin-1-yl)-3-methyl-pentan-1-one (2S,3S)-2-amino-1-(3,3-difluoro-pyrrolidin-1-yl)-3-methyl-pentan-1-one was prepared from 3,3-difluropyrrolidine hydrochloride and (L)-Boc-isoleucine, as analogously described in Example 7 (mp 195–198° C.).

Example 9

(S)-2-Amino-4-methyl-1-(3,3,4,4-tetrafluoro-pyrrolidin-1-yl)-pentan-1-one Hydrochloride (S)-2-amino4-methyl-1-(3,3,4,4-tetrafluoro-pyrrolidin-1-yl)-pentan-1-one hydrochloride was prepared from (L)-Boc-leucine and 3,3,4,4 tetrafluoropyrrolidine hydrochloride, as analogously described in Example 1 (mp>250° C.).

Example 10

(S)-2-Amino-2-cyclohexyl-1-(3,3-difluoro-azetidin-1-yl)-ethanone Hydrochloride (S)-2-amino-2-cyclohexyl-1-(3,3-difluoro-azetidin-1-yl)-ethanone hydrochloride was prepared by coupling 3,3-difluoro-azetidine hydrochloride (as described in WO 0047582) with Boc-(L)-cyclohexylglycine, followed by HCl deprotection as described in Example 1 (mp 220° C. dec.).

Example 11

(S)-2-Amino-1-(3,3-difluoro-azetidin-1-yl)-3-methyl-pentan-1-one Hydrochloride (S)-2-amino-1-(3,3-difluoro-azetidin-1-yl)-3-methyl-pentan-1-one hydrochloride was prepared by coupling 3,3-difluoro-azetidine hydrochloride (WO 0047582) with Boc-(L)-isoleucine followed by HCl deprotection as analogously described in Example 1 (mp 195° C. dec.).

Example 12

(S)-2-Amino-2-cyclohexyl-1-(4,4-difluoro-piperidin-1-yl)-ethanone Hydrochloride 4,4-Difluoro-piperidine hydrochloride, obtained by HCl treatment of 4,4-difluoro-piperidine-1-carboxylic acid tert-butyl ester (as described in WO0040561), was coupled with Boc-(L)-cyclohexylglycine followed by HCl deprotection, as analogously described in Example 1 (mp>250° C.).

Example 13

(S)-2-Amino-1-(4,4-difluoro-piperidin-1-yl)-3-methyl-pentan-1-one Hydrochloride (S)-2-amino-1-(4,4-difluoro-piperidin-1-yl)-3-methyl-pentan-1-one hydrochloride was prepared from 4,4-difluoro-piperidine hydrochloride and Boc-(L)-isoleucine as described in Example 1 (mp 190–192° C.).

Example 14

(S)-2-Amino-1-(3,3,4,4-tetrafluoro-pyrrolidin-1-yl)-propan-1-one Hydrochloride (S)-2-amino-1-(3,3,4,4-tetrafluoro-pyrrolidin-1-yl)-propan-1-one hydrochloride was prepared from Boc-(L)-alanine and 3,3,4,4-tetrafluoropyrrolidine as analogously described in Example 1 (mp>250° C.).

Alternative Preparation of 3,3,4,4-Tetrafluoropyrrolidine Hydrochloride

Step 1: Trifluoro-methanesulfonic Acid 2,2,3,3-Tetrafluoro-4-(trifluoro-methanesulfonvioxy)-butyl Ester.

To a cooled (0° C.) solution of 2,2,3,3-tetrafluorobutanediol (15 g, 93 mmol) and pyridine (19 mL, 230 mmol) in dichloromethane (250 mL), was added dropwise trifluoromethanesulfonic anhydride (34 mL, 200 mmol). After the addition, the mixture was stirred at 0° C. for one hour, followed by stirring at room temperature for one additional hour, then diluted with dichloromethane, washed with water and brine, dried over magnesium sulfate, filtered and concentrated to near dryness, leaving a dichloromethane-containing oil.

Step 2: 1-Benzyl-3,3,4,4-tetrafluoro-pyrrolidine Hydrochloride

A solution of the crude trifluoro-methanesulfonic acid 2,2,3,3-tetrafluoro-4-(trifluoro-methanesulfonyloxy)-butyl ester, benzylamine (10 mL, 93 mmol) and triethylamine (33 mL, 230 mmol) in ethanol (230 mL) was heated to reflux overnight. The mixture was concentrated to about one-third of its volume, diluted with ether, washed with 1 N sodium hydroxide, water and brine, dried over magnesium sulfate, filtered and concentrated to an oil. The oil was redissolved in ether, cooled to 0° C. and saturated with hydrogen chloride. The precipitate was collected and dried (23.8 g, 95%, (mp 139–143° C.).

Step 3: 3.3.4.4-Tetrafluoro-pyrrolidine Hydrochloride.

A solution of 1-benzyl-3,3,4,4-tetrafluoro-pyrrolidine hydrochloride (23.8 g, 88 mmol) in ethanol (300 mL) containing 10% palladium on carbon was treated with hydrogen in a Parr shaker at 45 psi for 3 hours. The mixture was filtered through Celite®, the filtrate was concentrated to dryness. The residue was triturated with ether and the solid was collected and dried (13.4 g, 85%, (mp 193–196° C.).

What is claimed is:

1. A compound of the Formula I,

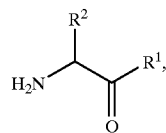

a prodrug thereof, or a pharmaceutically acceptable salt of the compound or the prodrug, wherein:

$R^1$ is 3-fluoroazetidin-1-yl, 3,3-difluoroazetidin-1-yl, 3,4-difluoropyrrolidin-1-yl, 3,3,4-trifluoropyrrolidin-1-yl, 3,3,4,4-tetrafluoropyrrolidin-1-yl, 3-fluoropiperidin-1-yl, 4-fluoropiperidin-1-yl, 3,4-difluoropiperidin-1-yl, 3,5-difluoropiperidin-1-yl, 3,3-difluoropiperidin-1-yl, 4,4-difluoropiperidin-1-yl, 3,4,5-trifluoropiperidin-1-yl, 3,3,4-trifluoropiperidin-1-yl, 3,3,5-trifluoropiperidin-1-yl, 3,4,4-trifluoropiperidin-1-yl, 3,4,4,5-tetrafluoropiperidin-1-yl, 3,3,4,4-tetrafluoropiperidin-1-yl 3,3,5,5-tetrafluoropiperidin-1-yl, 3,3,4,5,5-pentafluoropiperidin-1-yl, 3,3,4,4,5-pentafluoropiperidin-1-yl or 3,3,4,4,5,5-hexafluoropiperidin-1-yl; and $R^2$ is $(C_1-C_8)$alkyl or $(C_3-C_8)$cycloalkyl.

2. A compound of claim 1 wherein $R^1$ is 3-fluoroazetidin-1-yl or 3,3-difluoroazetidin-1-yl.

3. A compound of claim 1 wherein $R^1$ is 3,4-difluoropyrrolidin-1-yl, 3,3,4-trifluoropyrrolidin-1-yl, 3,3,4,4-tetrafluoropyrrolidin-1-yl.

4. A compound of claim 1 wherein $R^1$ is 3-fluoropiperidin-1-yl, 4-fluoropiperidin-1-yl, 3,4-difluoropiperidin-1-yl, 3,5-difluoropiperidin-1-yl, 3,3-difluoropiperidin-1-yl or 4,4-difluoropiperidin-1-yl.

5. A compound of claim 1 wherein $R^1$ is 3,4,5-trifluoropiperidin-1-yl, 3,3,4-trifluoropiperidin-1-yl, 3,3,5-trifluoropiperidin-1-yl, 3,4,4-trifluoropiperidin-1-yl, 3,4,4,5-tetrafluoropiperidin-1-yl, 3,4,4,5-tetrafluoropiperidin-1-yl, 3,3,4,4-tetrafluoropiperidin-1-yl 3,3,5,5-tetrafluoropiperidin-1-yl, 3,3,4,5,5-pentafluoropiperidin-1-yl, 3,3,4,4,5-pentafluoropiperidin-1-yl or 3,3,4,4,5,5-hexafluoropiperidin-1-yl.

6. A compound of claim 1 which is
(2S,3S)-2-amino-3-methyl-1-(3,3,4,4-tetrafluoro-pyrrolidin-1-yl)-pentan-1-one hydrochloride;
(2S,3S)-2-amino-1-(3-fluoro-azetidin-1-yl)-3-methyl-pentan-1-one hydrochloride;
(S)-2-amino-2-cyclohexyl-1-(3,3,4,4-tetrafluoro-pyrrolidin-1-yl)-ethanone hydrochloride;
(2S,3R)-2-amino-3-methyl-1-(3,3,4,4-tetrafluoro-pyrrolidin-1-yl)-pentan-1-one hydrochloride;
(S)-2-amino-2-cyclohexyl-1-(3-fluoro-azetidin-1-yl)-ethanone hydrochloride;
(S)-2-amino-3-methyl-1-(3,3,4,4-tetrafluoro-pyrrolidin-1-yl)-butan-1-one hydrochloride;
(S)-2-amino4-methyl-1-(3,3,4,4-tetrafluoro-pyrrolidin-1-yl)-pentan-1-one hydrochloride;
(S)-2-amino-2-cyclohexyl-1-(3,3-difluoro-azetidin-1-yl)-ethanone hydrochloride;
(2S,3S)-2-amino-1-(3,3-difluoro-azetidin-1-yl)-3-methyl-pentan-1-one hydrochloride;
(S)-2-amino-2-cyclohexyl-1-(4,4-difluoro-piperidin-1-yl)-ethanone hydrochloride;
(2S,3S)-2-amino-1-(4,4-difluoro-piperidin-1-yl)-3-methyl-pentan-1-one hydrochloride;
(S)-2-amino-1-(3,3,4,4-tetrafluoro-pyrrolidin-1-yl)-propan-1-one hydrochloride;
(S)-2-amino-1-(3,3-difluoro-azetidin-1-yl)-3-methyl-butan-1-one hydrochloride;
(S)-2-amino-1-(3-fluoro-azetidin-1-yl)-3-methyl-butan-1-one hydrochloride;
(2S,3R)-2-amino-1-(3-fluoro-azetidin-1-yl)-3-methyl-pentan-1-one hydrochloride;
(2S,3R)-2-amino-1-(3,3-difluoro-azetidin-1-yl)-3-methyl-pentan-1-one hydrochloride;
(S)-2-amino-2-cyclopentyl-1-(3,3-difluoro-azetidin-1-yl)-ethanone hydrochloride;
(S)-2-amino-2-cyclopentyl-1-(3-fluoro-azetidin-1-yl)-ethanone hydrochloride; or
(S)-2-amino-2-cyclopentyl-1-(3,3,4,4-tetrafluoro-pyrrolidin-1-yl)-ethanone hydrochloride.

7. A compound of claim 1 wherein the compound of Formula I,

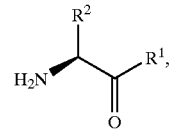

is a S enantiomer, as shown.

8. A pharmaceutical composition comprising a therapeutically effective amount of a compound of claim 1, a prodrug thereof or a pharmaceutically acceptable salt of the compound or the prodrug, and a pharmaceutically acceptable diluent or carrier.

9. A pharmaceutical composition comprising a therapeutically effective amount of
a first compound of claim 1, a prodrug thereof or a pharmaceutically acceptable salt of said compound or said prodrug; and
a second compound which is insulin or an insulin analog; insulinotropin; a biguanide; an $\alpha_2$-antagonist or an imidazoline; a glitazone; an aldose reductase inhibitor; a glycogen phosphorylase inhibitor; a sorbitol dehydrogenase inhibitor; a fatty acid oxidation inhibitor; an $\alpha$-glucosidase inhibitor; a $\beta$-agonist; a phosphodiesterase inhibitor; a lipid-lowering agent; an antiobesity agent; vanadate, a vanadium complex or a peroxovanadium complex; an amylin antagonist; a glucagon antagonist; a growth hormone secretagogue; a gluconeogenesis inhibitor; a somatostatin analog; an inhibitor of renal glucose; or an antilipolytic agent; a prodrug of the second compound or a pharmaceutically acceptable salt of the second compound or of the prodrug of the second compound.

10. A composition of claim 9 further comprising a pharmaceutically acceptable carrier or diluent.

11. A therapeutic method of inhibiting dipeptidyl peptidase-IV in a mammal, the method comprising administering to said mammal in need of inhibition of dipeptidyl peptidase-IV a therapeutically effective amount of a compound of claim 1, a prodrug thereof or a pharmaceutically acceptable salt of said compound or said prodrug.

12. A method of treating a condition mediated by dipeptidyl peptidase-IV inhibition in a mammal, the method comprising administering to said mammal suffering from a condition mediated by dipeptidyl peptidase-IV inhibition a therapeutically effective amount of a compound of claim 1, a prodrug thereof or a pharmaceutically acceptable salt of said compound or said prodrug.

13. The method of claim 12 wherein the condition treated is Type 2 diabetes, metabolic syndrome, hyperglycemia, impaired glucose tolerance, glucosuria, metabolic acidosis, cataracts, diabetic neuropathy, diabetic nephropathy, diabetic retinopathy, diabetic cardiomyopathy, Type 1 diabetes, obesity, a condition exacerbated by obesity, hypertension, hyperlipidemia, atherosclerosis, osteoporosis, osteopenia, frailty, bone loss, bone fracture, acute coronary syndrome, infertility due to polycystic ovary syndrome, disease progression in Type 2 diabetes, chronic fatigue, epilepsy, a disease associated with intestinal motility, ulcer, irritable bowel syndrome, inflammatory bowel syndrome, anxiety, depression, insomnia, chronic fatigue, epilepsy, an eating disorder, chronic pain or alcohol addiction.

14. The method of claim 13 wherein the condition treated is Type 2 diabetes.

* * * * *